United States Patent [19]

Kerwin et al.

[11] Patent Number: 5,736,098
[45] Date of Patent: Apr. 7, 1998

[54] METHOD FOR A SERVICING FLUID DISPOSAL SYSTEM

[75] Inventors: Michael John Kerwin; Jacky S. Yam, both of St. Louis, Mo.; Keith G. Korte, Damiansville, Ill.; Theodore J. Klefisch, Jr., Maryland Heights, Mo.

[73] Assignee: Sherwood Medical Company, St. Louis, Mo.

[21] Appl. No.: 439,019

[22] Filed: May 11, 1995

Related U.S. Application Data

[62] Division of Ser. No. 130,070, Sep. 30, 1993, Pat. No. 5,449,009.

[51] Int. Cl.⁶ .............. A61L 2/16; B08B 3/08; A61M 1/00
[52] U.S. Cl. .............. 422/28; 134/26; 134/37; 604/319
[58] Field of Search .............. 422/28, 317; 604/319, 604/326; 134/18, 26, 30, 37

[56] References Cited

U.S. PATENT DOCUMENTS

| | | | |
|---|---|---|---|
| 2,312,950 | 3/1943 | Zimarik | 68/17 |
| 2,647,384 | 8/1953 | Erlanger | 68/17 |
| 3,044,285 | 7/1962 | Koplin | 68/12 |
| 3,139,238 | 6/1964 | Norstrud et al. | 239/310 |
| 3,163,149 | 12/1964 | Ivey | 119/15 |
| 3,435,834 | 4/1969 | Cooper | 134/98 |
| 3,578,774 | 5/1971 | McDonald, Jr. | 128/227 |
| 3,645,283 | 2/1972 | Cassells | 134/58 DL |
| 3,653,234 | 4/1972 | Gillespie | 68/12 R |
| 3,707,160 | 12/1972 | Query | 137/209 |
| 3,802,447 | 4/1974 | Bender | 134/57 R |
| 3,804,297 | 4/1974 | Jurjans | 222/54 |
| 3,833,417 | 9/1974 | Griparis | 134/22 C |
| 3,836,329 | 9/1974 | Jordan | 134/37 X |
| 3,896,827 | 7/1975 | Robinson | 134/10 |
| 3,916,924 | 11/1975 | McGowan | 134/95 |
| 3,929,133 | 12/1975 | Ragab | 128/277 |
| 4,213,796 | 7/1980 | Shaffer | 134/26 |
| 4,277,290 | 7/1981 | Andrews et al. | 134/10 |
| 4,282,867 | 8/1981 | Du Toit | 128/66 |
| 4,307,741 | 12/1981 | Rossi | 134/100 |
| 4,646,768 | 3/1987 | Tanaka et al. | 134/167 R |
| 4,687,121 | 8/1987 | Copeland | 222/64 |
| 4,863,446 | 9/1989 | Parker | 604/317 |
| 4,865,814 | 9/1989 | Childress | 422/26 |
| 4,868,932 | 9/1989 | Thoma et al. | 4/323 |
| 4,905,325 | 3/1990 | Colditz | 4/321 |
| 4,915,119 | 4/1990 | Franklin | 134/57 R |
| 4,955,391 | 9/1990 | Parker et al. | 128/771 |
| 4,957,491 | 9/1990 | Parker | 604/317 |
| 5,242,434 | 9/1993 | Terry | 604/317 |

FOREIGN PATENT DOCUMENTS

3805609  9/1989  Germany.

*Primary Examiner*—Robert J. Warden
*Assistant Examiner*—E. Leigh McKane
*Attorney, Agent, or Firm*—Montgomery W. Smith; Grant D. Kang

[57] ABSTRACT

A fluid collection and disposal system which includes a reusable collection unit designed to be cleaned by a servicing unit after use. The servicing unit performs an automatic servicing cycle to remove the collected fluid from the collection unit and prepare it for reuse.

13 Claims, 4 Drawing Sheets

METHOD FOR A SERVICING FLUID DISPOSAL SYSTEM

This is a divisional of application Ser. No. 08/130,070 filed on Sep. 30, 1993, issued as U.S. Pat. No. 5,449,009.

BACKGROUND OF THE INVENTION

1. Field of the Invention

This invention relates to fluid disposal systems. More particularly, this invention relates to a system for disposing of body fluids and irrigants collected during surgical procedures.

2. Prior Art

The safe and convenient disposal of fluids collected during a surgical procedure in a manner which causes a minimal environmental impact has long been a difficult problem in the medical care industry. Presently, disposable suction canisters are used to collect body fluids during surgical procedures. Setup, use, handling and disposal of prior art suction canisters is often difficult and can place the health care workers and housekeeping personnel involved at risk of infection. For example, prior art procedures often include opening used canisters to dump the fluid into the sanitary sewer. This however is becoming an unacceptable risk to medical housekeeping personnel. Also, the prior art practice of incinerating the canisters, either after they have been emptied, or with the collected fluid remaining therein, is becoming an environmentally undesirable alternative.

Completely reusable fluid collection and disposal systems are an alternative to the use of disposable canisters for fluid collection and disposal. A system exemplary of the prior art of this type is shown in U.S. Pat. No. 4,863,446 to Parker. This system includes a collection unit for collecting fluids during a surgical procedure, and a treatment unit for coupling with the collection unit to remove and dispose of the collected fluids. The treatment unit is designed to couple with the collection unit to provide a washing solution to wash the collection unit and then drain the entire contents of the collection unit into the sanitary sewer. Although the Parker device may overcome several drawbacks of the prior art disposable canisters, it nevertheless has several drawbacks including difficulty in ensuring complete cleaning of the collection unit prior to reuse, difficulty in transporting and maneuvering the collection unit in the operating room when in use during a surgical procedure, and weight and bulkiness of the collection unit.

There is therefore a need in the art to develop a disposal system which reduces the potential exposure of medical personnel to contaminated or infectious fluids collected during a surgical procedure. There is also a need in the art to do this with minimum difficulty and maximum safety in servicing the collection unit prior to reuse thereof.

OBJECTS AND SUMMARY OF THE INVENTION

A principal object of the present invention is to provide a disposal system which safely and conveniently disposes of collected fluids.

Another object of the present invention is to minimize the health care worker's exposure to the collected fluid.

Another object of the present invention is to provide a disposal system which includes a servicing unit having an automatic servicing cycle designed to simplify user operation.

It is further an object of the present invention to provide a system which allows visual verification of proper servicing of a collection unit prior to its reuse.

These and other objects and advantages of the present invention are realized in a presently preferred embodiment thereof which provides for disposal of fluid in a safe and convenient manner. The invention provides a servicing unit for cleaning the collection unit in a manner which minimizes user exposure to potentially dangerous or infectious fluids.

In a presently preferred embodiment, shown by way of example and not necessarily by way of limitation, a disposal system made in accordance with the principals of the present invention is comprised of a reusable collection unit intended to collect fluids during a surgical procedure, a disposable manifold used in conjunction with the collection unit during collection of fluids, and a servicing unit for cleaning and applying disinfectant to the collection unit in preparation for its reuse.

The collection unit comprises a single collection vessel and site glass which is surrounded by a mostly transparent housing which allows easy viewing of the vessel, and which is covered with a vessel lid having a plurality of port openings for the attachment of the disposable manifold thereto during fluid collection. The port openings operate alternatively for attachment of the servicing unit to the collection unit for cleaning. The vessel lid is secured to the vessel by a top cover which includes a handle for convenience in transporting the collection unit.

The disposable manifold includes connection extensions for connection to the vessel lid of the collection unit during fluid collection in the OR. The manifold also includes a plurality of suction inlet ports for attaching suction lines through which fluid from the patient can be collected, and a vacuum outlet port to which a source of vacuum can be attached. The disposable manifold also includes an anti-reflux valve positioned between the suction inlet ports and the collection vessel which allows pressure balancing between the collection vessel and the site glass, and which prevents fluids from returning to the patient.

The servicing unit is preferably microprocessor controlled to automatically dump the collection unit contents to a sanitary sewer and thoroughly clean and properly apply an intermediate level of disinfectant to the collection unit and service unit fluid pathways. The servicing unit is designed to automatically accept the collection unit in proper position therein for servicing, and automatically lead the system through the proper sequence of events to empty, clean, and apply disinfectant to the collection vessel. Once the service cycle is completed, the servicing unit will allow release of the collection unit therefrom for reuse.

DETAILED DESCRIPTION OF THE PREFERRED EMBODIMENTS

As shown in the exemplary drawings for the purposes of illustration, an embodiment of a disposable system made in accordance with the principles of the present invention, referred to generally by the reference numeral 10, is provided for disposal of fluids collected during a surgical procedure.

Figure 1:
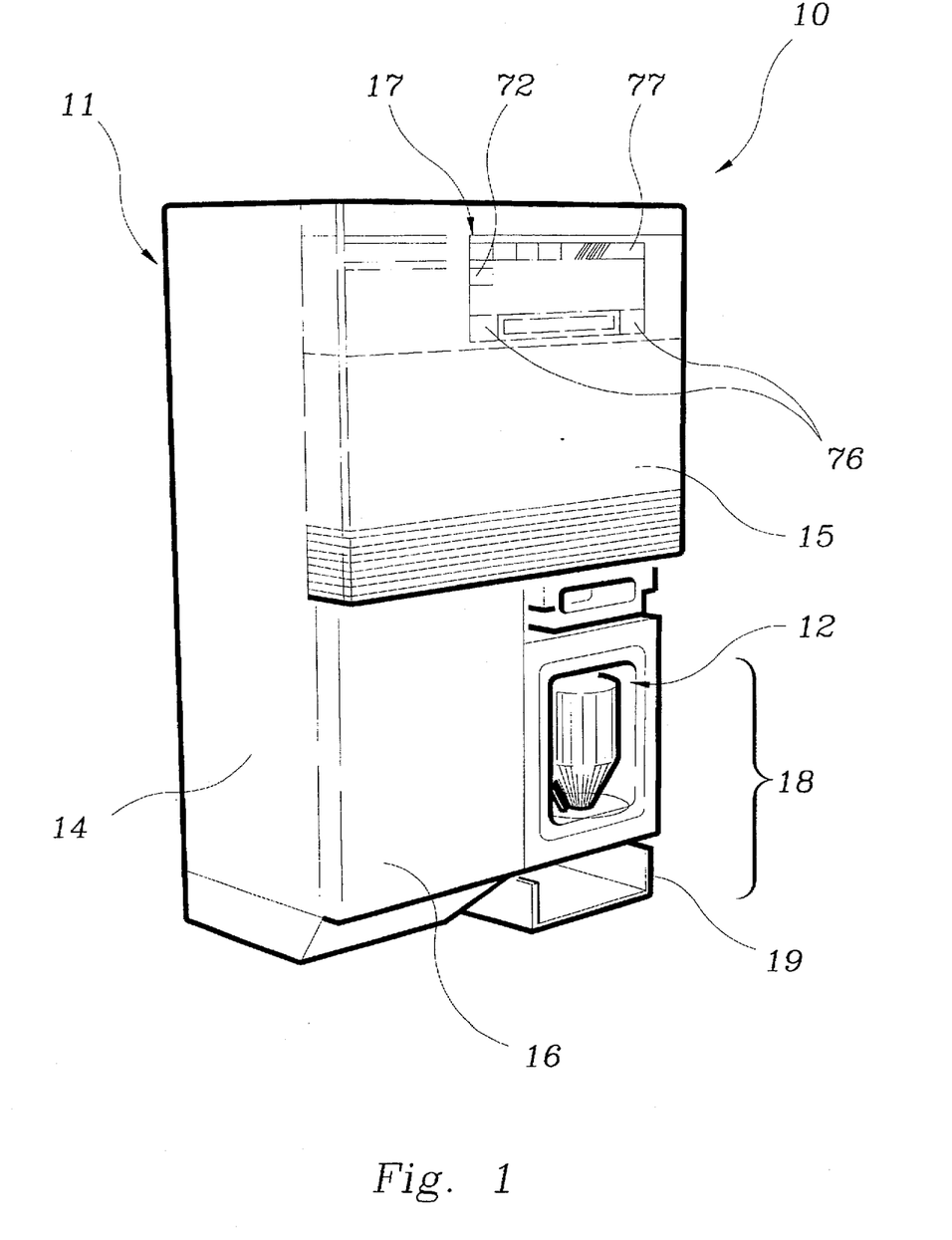
FIG. 1 is a perspective view of the servicing unit portion of the disposal system formed in accordance with the principles of the present invention with a collection unit positioned therein for servicing.
Figure 2:
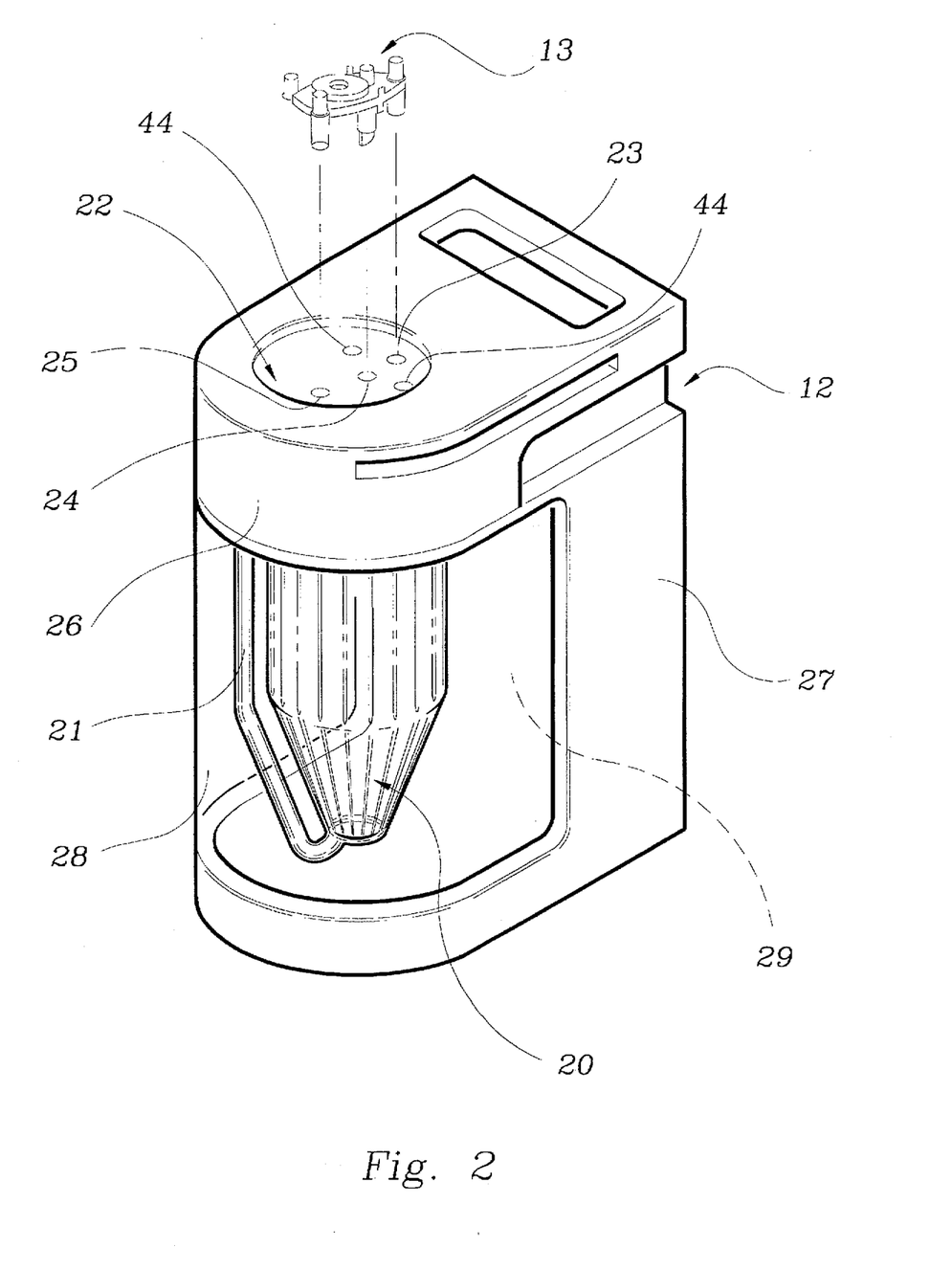
FIG. 2 is a perspective view of the collection unit and disposable manifold portions of the disposal system of the present invention.

More specifically, as shown in FIGS. 1 and 2, the principal components of the disposal system 10 include a servicing unit 11, a collection unit 12, and a disposable manifold 13. The servicing unit 11 comprises a generally rectangular housing 14 having a front panel 15 and a storage door 16. The storage door 16 covers a storage compartment (not shown) suitable for storing quantities of detergent and/or disinfectant. The front panel 15 includes a display 17 which is used to inform the operator of the status of operation of the servicing unit 11. A docking station 18 is also included in the servicing unit 11 which includes a lifting mechanism 19 and is sized to receive a collection unit 12 for servicing as shown.

Referring now to FIG. 2, the collection unit 12 comprises a vessel 20 which is preferably generally cylindrical in shape with a conically shaped bottom piece. A site glass 21 is preferably formed integrally with the vessel 20 and may have graduated markings thereon or thereabout which indicate the volume of fluid collected in the vessel 20. The top of the vessel 20 is covered with a vessel lid 22 which is preferably slightly concaved on its upper surface to ensure that any unlikely fluid leaks can be contained and easily cleaned.

The vessel lid 22 includes three openings therethrough which extend into the vessel 20. Two of these openings have a dual function depending on whether fluid is being collected into the vessel 20 during a surgical procedure, or whether the collection unit 12 is being serviced by the servicing unit 11. In the first instance, port 23 operates as the vacuum connection port to supply a source of suction to the vessel 20, and the port 24 operates as a patient fluid inlet port through which fluid collected from the patient is drawn by suction into the vessel 20. Port 25 is in fluid flow connection with the site glass 21 and is closed to the atmosphere during fluid collection.

During servicing of the collection unit 12, the ports 23 and 24 operate as inlet ports for passage of cleaning fluids into the vessel 20, and the port 25 operates as an outlet port to allow collected body fluids, and subsequent cleaning fluids, to be withdrawn from the vessel 20 by operation of the servicing unit 11 and disposed of thereby into a sanitary sewer.

The vessel lid 22 is securely held to the vessel 20 by the top cover 26, which itself is secured to the frame 27. The frame 27 surrounds the vessel 20 and includes a transparent optical shield 28 and a rear window 29 through which the vessel 20 and the site glass 21 can be easily viewed. The rear window 29 allows backlighting into the collection unit 12 to aid in viewing the contents of the vessel 20 through the transparent optical shield 28 during collection, and to aid in viewing the site glass 21 and volume graduation thereon.

Referring momentarily to FIG. 1, the rear window 29 also allows viewing of the vessel 20 even when the collection unit 12 is mounted for servicing in the docking station 18 of the servicing unit 11. This allows the operator to visually ensure that the servicing unit 11 is properly performing its automatic service cycle on the collection unit 12 and that the vessel 20 is actually emptied of fluid and appears clean at the end of the automatic servicing cycle.

The disposable manifold 13 is attached to the collection unit 12 when fluids are being collected from a patient during surgery. A detailed description of the structure and operation of the manifold 13 is presented in co-pending U.S. patent application Ser. No. 08/032,946 filed Mar. 17, 1993 titled "Fluid Collection and Disposal System" which is incorporated herein by reference.

Figure 3:
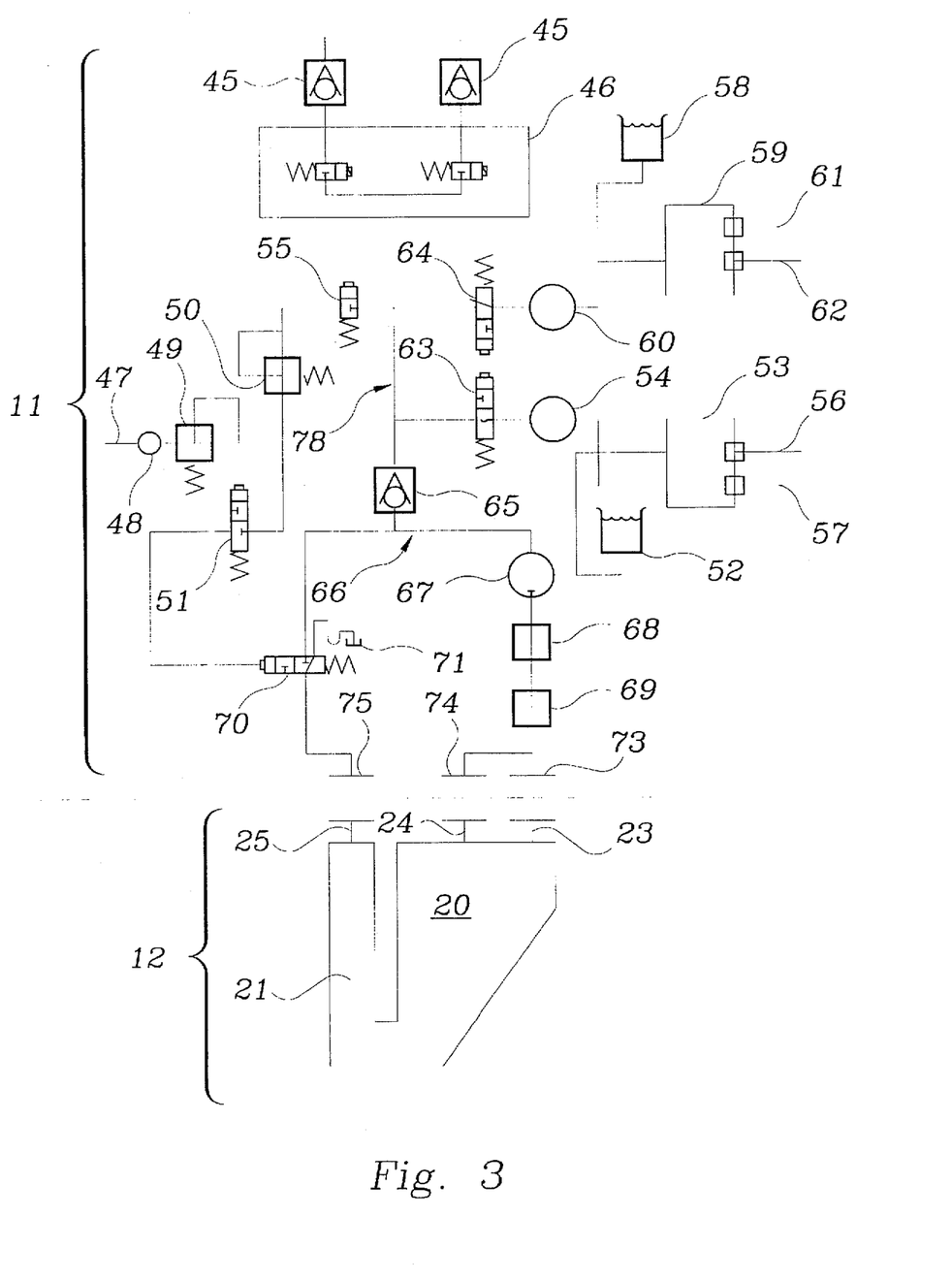
FIG. 3 is a schematic view of the servicing unit and collection unit portions of the disposal system of the present invention.

FIG. 3 shows a schematic view of the fluid flow path through the servicing unit 11 and the collection unit 12. Hot and cold water enter the servicing unit 11 through non-sanitary check valves 45 and pass through a mixing valve 46. Compressed air enters the servicing unit 11 through line 47 and immediately passes through the filter 48 to the compressed air regulator 49. The compressed air branches to pass in a first direction through a second regulator 50 and valve 55, and a second direction through valve 51. Detergent enters the system from detergent reservoir 52 and passes through metering chamber 53 and metering pump 54. The metering chamber 53 includes maximum and minimum level sensors 56 and 57 respectively.

The disinfectant enters the servicing unit 11 in a similar manner by passing from disinfectant reservoir 58 through the metering chamber 59 and metering pump 60. The metering chamber 59 also includes maximum level and minimum level sensors 61 and 62 respectively. Valves 63 and 64 separate the detergent reservoir and disinfectant reservoir from the main line 78. The sensors signal the microprocessor of the servicing unit 11 which automatically validates delivery of the proper amount of detergent and disinfectant to the main line 78.

Once the cleaning or disinfection fluid moves past the sanitary check valve 65, it enters the sanitary circuit 66. A circulating pump 67, such as a centrifugal pump, is positioned in the sanitary circuit 66 just upstream of pressure sensor 68 and temperature sensor 69. The divert valve 70 is also positioned in the sanitary circuit 66. The divert valve 70, when opened, diverts fluid flow through the sanitary circuit 66 into the sanitary sewer drain 71. Sanitary circuit line extensions 73, 74 and 75 are sized and designed to be insertable into the ports 23, 24 and 25 respectively of the collection vessel 12 through the vessel lid 22 in a fluid-tight connection.

Figure 4:
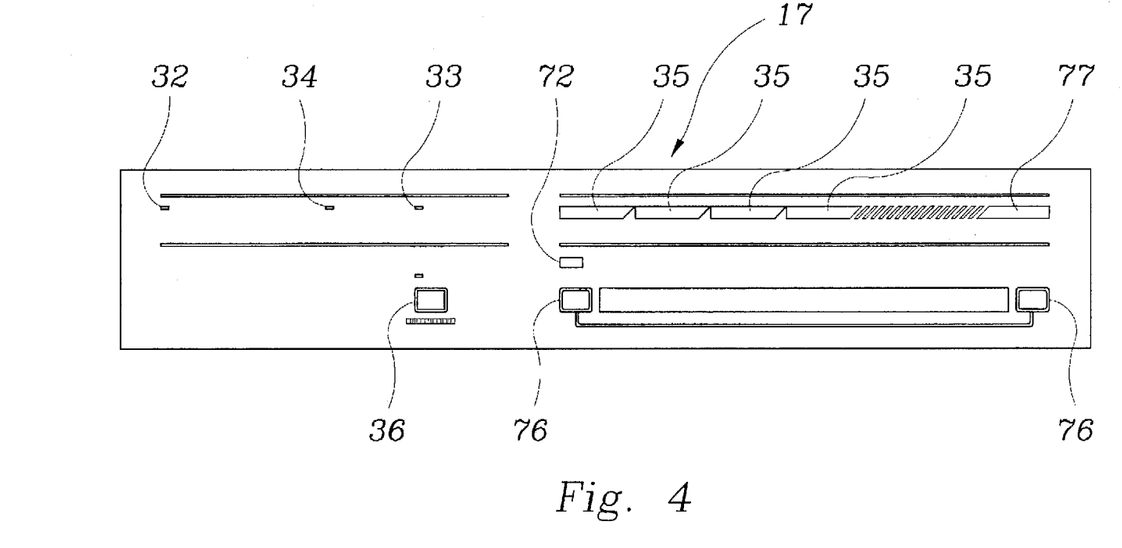
FIG. 4 is an enlarged view of the front panel of the servicing unit made in accordance with the principles of the present invention.

Referring now to FIG. 4, the front panel display 17 of the servicing unit 11 includes a low disinfectant level indicator 33 and low detergent level indicator 34 which will activate when the liquid level is insufficient for another service cycle. A system defect indicator 32 will activate in response to an operational defect in the servicing unit 11. Finally, cycle process indicators 35 and "system ready" indicator 72 will activate at appropriate stages in the servicing cycle. Detailed operation of the indicators on the front panel 17 of the servicing unit 11 will be explained below in connection with operation of the servicing unit.

As a result of the servicing units minimal user interface design, only two functions will be made available on the service unit front panel 17 for the user. These functions include activation of the lift mechanism 19 by means of push buttons 76, and emergency shut down of the servicing unit 11 by activation of the "interrupt" push button 36.

The lift mechanism push buttons 76 are located at approximately the eye level of the user, and separated by a distance to assure that the user must use both hands (one hand for each push button 76) in order to activate the lifting mechanism 19. This is a safety measure to keep the user's hands free from entanglement with the lift mechanism 19, and from the surface of the collection unit 12 as it is engaging the servicing unit 11. The electrical output of the two lift mechanism push buttons 76 are wired in series, so that the lift mechanism 19 will operate only when both push buttons are pressed simultaneously. If one or both of the push buttons 76 are released during lift activation, the lift mechanism 19 will stop. Operation will only continue when both push buttons 76 are again pressed.

Further, the push buttons 76 are programmed to activate the lift mechanism 19 only at predefined stages of the servicing cycle. Specifically, activation of the lift mechanism push buttons 76 at the beginning of an automatic servicing cycle will only operate to raise the collection unit 12 in order to attach the collection unit 12 to the servicing unit 11. At the end of the automatic servicing cycle, activation of the push buttons 76 will only operate to lower the collection unit 12.

Activation of the "interrupt" push button 36 will halt processing of the collection unit 11 immediately at the particular stage of the service cycle in process at the time of its activation. Once the "interrupt" push button 36 is activated, the collection unit 12 will be held in the completely engaged position with the servicing unit 11 until the reset switch 37 (see FIG. 5) on the service panel 31 is activated.

Figure 5:
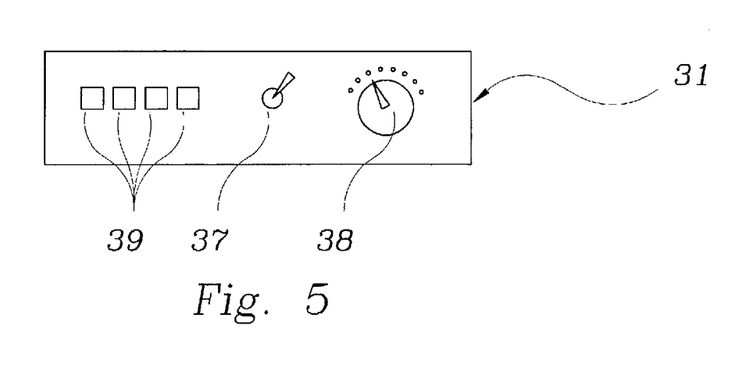
FIG. 5 is an enlarged view of the service panel of the servicing unit made in accordance with the principles of the present invention.

As shown in FIG. 5, the service panel display 31 includes the manual reset switch 37. Activation of the reset switch 37 will operate to cause the servicing unit 11 to proceed directly to the end of the servicing cycle and activate the cycle completion indicator 77 on the front panel display 17. This stage of the service cycle enables the lift mechanism 19 to be activated by the push buttons 76, which activation causes the lifting mechanism 19 to lower the collection unit 12 downwardly to disengage it from the servicing unit 11. Activation of the reset switch 37 will also clear the interrupt and deactivate the system defect indicator 32 which was automatically activated whenever the "interrupt" push button 36 was pressed or a system malfunction was identified. The servicing unit 11 will thereafter be capable of resuming normal operation, until it again detects a system malfunction or the "interrupt" push button 36 is again activated.

The service panel 31 also includes a multiposition water temperature switch 38 to allow selection of the optimum water temperature used by the servicing unit 11 during the servicing cycle.

The service panel 31 further includes a series of four indicators, preferably LED's, which will illuminate a binary code corresponding to a particular malfunction of the servicing unit 11 detected during a servicing cycle. The malfunction code indicators 39 will display a binary code corresponding to malfunctions such as: system microprocessor malfunctions; failure of a diagnostic pressure test due to a damaged collection vessel 12 or a faulty seal in the servicing unit fluid flow pathways; an inadequate water/air pressure or temperature; an inaccurate valve position; an incorrect position of the lifting mechanism 19; or an occlusion in a fluid flow pathway. Any of the above conditions can be sensed by the above described sensors included in the servicing unit 11 and will prevent proper system operation. After the malfunction has been corrected, the reset switch 37 can be activated to reset the servicing unit 11 to resume normal operation. Should multiple malfunctions be detected simultaneously, the appropriate malfunction codes will be displayed on the malfunction code indicators in two second intervals in order to allow servicing personnel to recognize and correct each malfunction.

It is intended that the service panel display 31 be positioned within the servicing unit 11 such that it cannot be readily accessed by the user of the servicing unit 11. Instead, it is intended that the service panel display 31 be accessed only by specially qualified personnel.

Various proximity sensors (not shown) are also preferably included as part of the servicing unit 11. Specifically, proximity sensors for validating the up or down positions of the lift mechanism 19, the open and closed positions of the divert valve 71, and the presence or absence of a collection unit 12 within the lift mechanism 19 are included.

SYSTEM OPERATION

Operation of the disposal system to effect collection of fluids from a patient and subsequent servicing of the collection unit 12 to thoroughly cleanse the interior of the vessel 20, dispose of the fluids from the vessel 20 to the sanitary sewer, and apply a disinfectant to the interior surfaces of the vessel 20 and the sanitary circuit 66, will now be explained.

Prior to use of the collection unit 12 for collecting fluid, a disposable manifold 13 must first be placed in its proper position on the vessel lid 22 in order to attach the collection unit 11 to a suction source and to collect fluid from a patient.

A detailed explanation of the manner in which the manifold 13 operates with the collection unit 12 to collect fluid from a patient is presented in the above-mentioned copending U.S. patent application Ser. No. 08/032,946.

Once fluid collection is completed, the vacuum source and patient suction lines are disconnected from the manifold 13. The collection unit 12 is then transported to the servicing unit 11 with the disposable manifold 13 still in place thereon.

Before the collection unit 12 can be inserted into the servicing unit 11, the disposable manifold 13 must be removed. Referring again to FIG. 1, if a previously processed collection unit 12 has been removed from the servicing unit docking station 18, the docking station 18 will be unobstructed and the "ready" indicator 72 on the display 17 will be activated. The user can then push the collection unit 12 into the service unit docking station 18 until it is completely inserted in the manner shown in FIG. 1. A proximity sensor (not shown) ensures that the collection unit 12 is properly positioned within the docking station 18 before the lifting mechanism 19 can be activated.

The user then initiates a servicing cycle by pressing the two push buttons 76 which are preferably spaced a sufficient distance apart on the display 17, that both of the operator's hands are required for their activation. Upon initiation, the collection unit 12 is raised by the lifting mechanism 19 until the sanitary circuit line extensions 73, 74 and 75 (as shown in FIG. 3) of the servicing unit 11 are seated in the ports 23, 24 and 25 respectively of the collection unit 12 in a fluid-tight fit. It is preferred that the operator be required to continue holding both push buttons 76 until the lifting mechanism 19 reaches its maximum height. If one or more of the buttons 76 are prematurely released, the lifting mechanism 19 will stop. This is an important safety feature which prevents accidental placement of hands between the servicing unit 11 and the collection unit 12 while the lifting mechanism 19 is in operation.

Once the maximum height of the lifting mechanism 19 is reached, the servicing unit 11 is preprogrammed to allow it to automatically control and complete the remainder of the service cycle unattended by the operator. If a problem in the automatic servicing cycle is detected by the servicing unit 11, it automatically shuts down servicing operations and signals the operator that a problem has occurred by activating the "system defect" indicator 32 on the front panel display 17. The servicing unit microprocessor then downloads the malfunction information to the service panel 31 for assistance to a servicing technician in correcting the malfunction.

Preprogrammed servicing begins with a series of self diagnostics. First, a verification of the proper valve positions throughout the servicing unit 11, proper operation of the pressure and temperature sensors, and adequate volumes of detergent and disinfectant chemicals and priming of the chemical flow lines is conducted.

Next, in order to verify that the collection unit 12 is properly connected to the internal plumbing of the servicing unit 11, the divert valve 70 is closed to the drain 71 and compressed air is injected into the entire sanitary circuit 66 until a minimum pressure of 5 psig is sensed in the sanitary circuit 66. After a short time interval, pressure is again sensed. If the difference between the two pressure readings is acceptable to assure that the vessel is not cracked and that all connections are properly sealed, the cycle will continue. If the difference between the two pressure readings is greater than a predetermined acceptable limit, system operation will halt and the "system defect" indicator 32 will be activated. The servicing code which indicates a leak in the sanitary circuit 66 causing a pressure test failure will be sent to the service display 31.

If the pressure test readings are acceptable, the vessel is then purged. To accomplish this, the divert valve 70 is moved to its open position by opening valve 51 to allow compressed air to pass to operate the divert valve 70. Compressed air is then forced through the sanitary circuit 66 into the vessel 20 by opening valve 55, thus forcing fluid therein up the site glass 21 through the port 25 and past the divert valve 70 into the drain 71. After forcing air for a minimum of three seconds through the sanitary circuit 66, pressure in the circuit 66 is continuously monitored by pressure sensor 68. The forced air will be terminated when the pressure falls below a predetermined level, such as one psig, which indicates that the fluid has been completely forced into the drain 71. If the sanitary circuit 66 cannot be purged due to blockage or occlusion therein, cycle operation will be halted and the "system defect" indicator 32 will be activated with the proper coded description of the defect being sent to the malfunction code indicators 39 on the service panel 31.

Next, an initial warm water rinse and purge is performed by opening the divert valve 70 and engaging the circulation pump 67. The cold and hot water valves 46 are then opened for a predetermined period of time to force the warm water mixture into the sanitary circuit 66 to rinse the vessel 20 and site glass 21 and allow the water to pass into the drain 71. The time period for the warm water rinse is preferably approximately 12 to 15 seconds. The water temperature is monitored to ensure that the temperature is within a predetermined acceptable range, such as approximately between 90° F. and 120° F. The pressure at pressure sensor 68 is also monitored to ensure that the water pressure within the circuit 66 remains within predetermined limits, such as approximately between 20 and 30 psig when both the hot and cold water valves 46 are open, and between 8 and 15 psig if only the hot water valve 46 is open. If pressure or temperature are outside of the predetermined limits, operation of the cycle will be halted and the "system defect" indicator 32 will be actuated with the proper error code being displayed in the service panel 31 as explained above.

After the initial warm rinse is completed, the vessel 20 is again purged by injection of compressed air for a minimum of three seconds and continues until all liquid is forced into the drain 71 in the same manner as the air purge procedure described above.

The warm water rinse and purge subcycle is preferably repeated a predetermined number of iterations, preferably approximately 6 to 7 iterations to extend the entire warm water rinse and purge cycle to approximately a 90 second time period. The plural iterations of the relatively short warm rinse and purge subcycle operates to keep the vessel water level low which in turn, permits greater dispersion of the water over the interior surface area of the vessel 20 and subsequently better rinsing performance.

Once the warm water rinse and purge cycles are complete, the divert valve 70 is closed and the detergent metering pump 54 is activated to deliver a preselected volume of detergent into the sanitary circuit 66. The level sensors 56 and 57 will verify detergent injection and if a failure is sensed, operation of the cycle will be halted and the error will be indicated as described above. Warm water is then injected into the fluid circuit 66 until the pressure reaches a predetermined level, such as approximately five psig, which corresponds to approximately 3 liters of water in the fluid circuit 66. The water temperature is again monitored to ensure that it falls within a predetermined range, preferably approximately 90° to 140° F., with an ideal preferred temperature of approximately 110° F. Hot and cold water valves 46 will be opened at predetermined time intervals to ensure proper temperature based on data collected during initial warm rinse cycles.

The circulating pump 67 continues to circulate the detergent solution in the sanitary circuit 66 for a predetermined period of time. The circulating pump 67 is then disengaged and no action is taken by the servicing unit 11 for another predetermined period of time. This "holding" period is to allow the detergent to stand in the vessel 20 and site glass 21 for the holding period to allow further cleaning thereof and the dispersion of detergent bubbles. The divert valve 70 is thereafter again opened and the circuit 66 is air purged in the manner described above in order to force the detergent solution into the drain 71.

Next, another hot water rinse and purge is performed to thoroughly rinse the vessel 20 after the detergent circulation and purge.

As a final step to assure vessel cleanliness, the divert valve 70 is again closed and the circuit 66 is injected with hot water until the pressure in the circuit 66 is approximately 5 psi, which corresponds to approximately 3 liters of water. The water is preferably at a temperature between 110° and 145° F. The hot water is then circulated through the sanitary circuit 66 for a predetermined period of time, such as approximately 1 to 2 minutes, by engaging the circulation pump 67. After the circulation period is completed, the divert valve 70 is again opened and the circuit 66 is air purged to force the water into the drain 71 in the manner as explained above.

Once the cleaning subcycle is completed, the disinfecting subcycle begins. The disinfectant metering pump 60 is activated to inject a preselected volume of disinfectant into the sanitary circuit 66, with the proper amount of disinfectant delivery being monitored by the level sensors 61 and 62.

The divert valve 70 is then closed and the hot and cold water valves 46 are opened to allow injection of water into the fluid circuit 66 to a pressure of approximately 5 psig which corresponds to approximately 3 liters of water at a temperature preferably between 80° and 150° F., ideally 125° F. The circulation pump 67 is then engaged for a predetermined period, preferably 1 to 2 minutes, to circulate the disinfectant solution in the fluid circuit 66 to thoroughly apply disinfectant to the interior surfaces of the entire fluid circuit 66 including the collection vessel 20 and site glass 21. The divert valve 70 is then opened and an air purge is initiated to force the disinfectant solution into the drain 71.

At this point, another "hold" period is initiated for a predetermined amount of time, preferably at least 10 minutes, in order to ensure that the disinfectant remains in contact with the interior surfaces of the sanitary circuit 66 a sufficient amount of time to ensure maximum effectiveness of the disinfectant. This holding period also allows time for bubbles or the like to collapse and migrate to the bottom of the vessel 20 where they can be quickly air purged to the drain after the holding period is completed in the manner as has been described above. If desired, this final air purge may in fact be a series of short air purges occurring at spaced time intervals during the "hold" period.

At the end of the final purge after the disinfectant holding period, the automated portion of the servicing cycle is complete. The end of the servicing cycle will be indicated on the servicing unit front panel 17 by activation of the "cycle complete" indicator 77. To remove the processed collection unit 12 from the servicing unit 11, the user then presses the two push buttons 76 that activate the lift mechanism 19. The push buttons 76 must be pressed continuously until the collection unit 12 is completely lowered. The collection unit 12 can then be removed from the servicing unit 11 and is ready for reuse.

If at any time the detergent or disinfectant levels are sensed to be too low for a proper operation of an automatic servicing cycle, the low detergent and/or low disinfectant indicators 34 and 33 respectively will be activated. The appropriate chemical supply must then be replenished before another servicing cycle can be initiated.

If an emergency situation occurs at any time during a servicing cycle, and the user determines that the servicing cycle must be halted, the user can press the "interrupt" push button 36. Servicing of the collection unit 12 will stop immediately thereafter when the servicing unit reaches a safe condition when all motors are disengaged, the divert valve 70 is opened to drain, and the collection unit 12 is properly held in its uppermost position by the lift mechanism 19. Thereafter, the user will not be able to restart operation of the servicing unit 11 from the front control panel 17. Instead, it is intended that only specially trained personnel will be able to restart the servicing unit 11. The restart and resetting of the servicing unit 11 is accomplished by accessing the service panel 31 and toggling the reset switch 37.

The cycle process indicators 35 located on the front panel 17 of the servicing unit 11 are intended to indicate the four stages in the progress of the servicing cycle. Each indicator 35 will clearly signal the user the stage of the servicing cycle presently being carried out. For example, the cycle processing indicators 35 may include a series of 4 indicators which correspond to an initial or "ready" stage of the cycle, a purge or rinse "step 1" of the servicing cycle, a detergent wash "step 2" of the servicing cycle, and a disinfectant application "step 3" of the servicing cycle. The "cycle complete" indicator 77 is activated after all of the cycle process indicators 35 have been activated in their proper turn and the servicing cycle is complete. In the event of a system error, the cycle progress indicators 35 remain activated thus indicating in which stage of the automatic servicing cycle the error occurred so as to aid in correction of the malfunction.

It will be apparent from the foregoing that, while a particular embodiment of the invention has been illustrated and described, various modifications can be made thereto without departing from the spirit and scope of the invention. Accordingly, it is not intended that the invention be limited, except as by the appended claims.

We claim:

1. A method of servicing a fluid collection unit with a servicing unit, the method steps comprising:
   inserting a fluid collection unit into a stationary docking portion of a servicing unit,
   cycling the servicing unit through an automatic servicing cycle to clean the fluid collection unit, the servicing cycle comprising the steps of:
      purging with a fluid force the fluid collection unit of any fluid content,
      rinsing the fluid collection unit with a rinsing fluid,
      purging with a fluid force the fluid collection unit of the rinsing fluid, and
      removing the fluid collection unit from the servicing unit;
   wherein the fluid collection unit remains stationary throughout said automatic servicing cycle.

2. A method according to claim 1, wherein said step of cycling the servicing unit through an automatic servicing cycle further includes the step of performing a diagnostic check of the operability of the servicing unit prior to beginning the servicing cycle.

3. A method according to claim 2 wherein said step of performing a diagnostic check includes performing a pressure check of the servicing unit to ensure that no fluid leakage will occur from the servicing unit or fluid collection unit during the automatic servicing cycle.

4. A method according to claim 3 wherein said automatic servicing cycle further includes a step of applying a disinfectant to the fluid collection unit after the step of rinsing and purging added in claim 3.

5. A method according to claim 1 wherein said steps of purging and rinsing the fluid collection unit constitute a purge and rinse subcycle of the automatic servicing cycle of the servicing unit and the purge and rinse subcycle is repeated a plurality of times in series during the automatic servicing cycle.

6. A method according to claim 1, wherein said automatic servicing cycle further includes the step of washing the fluid collection unit with a detergent solution after the step of purging, rinsing, and purging the fluid collection unit.

7. A method according to claim 6, wherein said automatic servicing cycle further includes a step of rinsing and purging after the step of washing the fluid collection unit with a detergent solution.

8. A method according to claim 1, wherein said automatic servicing cycle further includes the step of applying a disinfectant to the fluid collection unit after the step of purging, rinsing, and purging the fluid collection unit.

9. A method according to claim 8 wherein said step of applying a disinfectant to the fluid collection unit further includes pausing said automatic servicing cycle for a predetermined time period after application of disinfectant to the fluid collection unit to increase the dwell time of the disinfectant on the collection unit.

10. A method according to claim 1, wherein said step of inserting a fluid collection unit into a stationary docking portion of the servicing unit further includes the step of inserting the fluid collection unit into a lift mechanism of the servicing unit and activating the lift mechanism to position the fluid collection unit within the servicing unit for servicing.

11. A method according to claim 10 wherein said step of activating the lift mechanism requires continuous user activation of the lift mechanism until the fluid collection unit is completely positioned for servicing in the servicing unit.

12. A method according to claim 1, wherein said step of purging is accomplished by forcing compressed air into the fluid collection unit.

13. A method of servicing a fluid collection unit with a servicing unit, the method steps comprising:

inserting a fluid collection unit at least partially into a servicing unit, cycling the servicing unit through an automatic servicing cycle to clean the fluid collection unit, the servicing cycle comprising the steps of:

purging with a fluid force the fluid collection unit of any fluid content, rinsing the fluid collection unit with a rinsing fluid, purging with a fluid force the fluid collection unit of the rinsing fluid, and removing the fluid collection unit from the servicing unit, said step of inserting a fluid collection unit at least partially into the servicing unit further including the step of inserting the fluid collection unit into a lift mechanism of the servicing unit and activating the lift mechanism to position the fluid collection unit within the servicing unit for servicing, said step of activating the lift mechanism requiring continuous user activation of the lift mechanism until the fluid collection unit is completely positioned for servicing in the servicing unit.

* * * * *